US009265560B2

(12) United States Patent
Johnston

(10) Patent No.: US 9,265,560 B2
(45) Date of Patent: Feb. 23, 2016

(54) SYSTEM AND METHOD FOR DETECTING AND SUPPRESSING ARC FORMATION DURING AN ELECTROSURGICAL PROCEDURE

(75) Inventor: Mark A. Johnston, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1400 days.

(21) Appl. No.: 13/034,822

(22) Filed: Feb. 25, 2011

(65) Prior Publication Data

US 2012/0220997 A1 Aug. 30, 2012

(51) Int. Cl.
*A61B 18/12* (2006.01)
*A61B 17/00* (2006.01)
*A61B 18/00* (2006.01)
*A61B 18/14* (2006.01)

(52) U.S. Cl.
CPC ......... *A61B 18/1206* (2013.01); *A61B 18/1233* (2013.01); *A61B 18/1442* (2013.01); *A61B 2017/00154* (2013.01); *A61B 2018/0063* (2013.01); *A61B 2018/0072* (2013.01); *A61B 2018/00577* (2013.01); *A61B 2018/00678* (2013.01); *A61B 2018/00726* (2013.01); *A61B 2018/00827* (2013.01)

(58) Field of Classification Search
CPC ...... A61B 18/04; A61B 18/042; A61B 18/08; A61B 18/082; A61B 18/10; A61B 18/12; A61B 18/1206; A61B 18/1233; A61B 18/14; A61B 18/1482; A61B 18/1492; A61B 2018/00577; A61B 2018/00601; A61B 2018/00589; A61B 2018/0063; A61B 2018/00648; A61B 2018/00702; A61B 2018/00726; A61B 2018/00755; A61B 2018/00779; A61B 2018/00791; A61B 2018/00827; A61B 2018/00892; A61B 2018/00922; A61B 2018/1213; A61B 17/00; A61B 17/00234; A61B 17/32
USPC ...................................................... 606/33–50
See application file for complete search history.

(56) References Cited

U.S. PATENT DOCUMENTS

| 3,923,063 | A | 12/1975 | Andres et al. |
| 4,196,734 | A | 4/1980 | Harris |
| 4,429,694 | A | 2/1984 | McGreevy |
| 4,651,264 | A | 3/1987 | Shiao-Chung Hu |
| RE34,432 | E | 11/1993 | Bertrand |

(Continued)

FOREIGN PATENT DOCUMENTS

| DE | 179607 | 3/1905 |
| DE | 1099658 | 2/1961 |

(Continued)

OTHER PUBLICATIONS

European Search Report for European Application No. 12157141.8 dated Jun. 18, 2012.

(Continued)

*Primary Examiner* — Michael Peffley
*Assistant Examiner* — Khadijeh Vahdat

(57) ABSTRACT

A method for suppressing arc formation during an electrosurgical tissue treatment procedure includes the steps of supplying pulsed current from an energy source to tissue and measuring the pulsed current supplied from the energy source. The method also includes the steps of comparing an instantaneous measured pulse to a predetermined threshold and controlling the pulsed current supplied from the energy source based on the comparison between the instantaneous measured pulse and the predetermined threshold.

13 Claims, 4 Drawing Sheets

(56) References Cited

U.S. PATENT DOCUMENTS

| | | | |
|---|---|---|---|
| 5,267,994 | A | 12/1993 | Gentelia et al. |
| 5,472,443 | A | 12/1995 | Cordis et al. |
| 5,971,980 | A | 10/1999 | Sherman |
| 5,976,128 | A | 11/1999 | Schilling et al. |
| 6,142,992 | A * | 11/2000 | Cheng et al. .................. 606/34 |
| 6,261,286 | B1 | 7/2001 | Goble et al. |
| 6,293,942 | B1 | 9/2001 | Goble et al. |
| 6,306,134 | B1 | 10/2001 | Goble et al. |
| 6,364,877 | B1 | 4/2002 | Goble et al. |
| 6,416,509 | B1 | 7/2002 | Goble et al. |
| 6,740,079 | B1 | 5/2004 | Eggers et al. |
| 6,784,405 | B2 | 8/2004 | Flugstad et al. |
| 6,923,804 | B2 | 8/2005 | Eggers et al. |
| 7,004,174 | B2 | 2/2006 | Eggers et al. |
| 7,303,557 | B2 | 12/2007 | Wham et al. |
| 7,364,577 | B2 | 4/2008 | Wham et al. |
| D574,323 | S | 8/2008 | Waaler |
| 7,651,492 | B2 | 1/2010 | Wham |
| 7,678,105 | B2 | 3/2010 | McGreevy et al. |
| 2002/0151884 | A1 | 10/2002 | Hoey |
| 2002/0165531 | A1 | 11/2002 | Goble |
| 2006/0161148 | A1 | 7/2006 | Behnke |
| 2009/0082765 | A1 | 3/2009 | Collings et al. |
| 2009/0259224 | A1 | 10/2009 | Wham et al. |
| 2012/0010610 | A1 * | 1/2012 | Keppel ........................... 606/39 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1681026 A2 | 7/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/053532 | 5/2008 |

OTHER PUBLICATIONS

U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/566,173, filed Sep. 24, 2009, James A. Gilbert.
U.S. Appl. No. 12/566,233, filed Sep. 24, 2009, William N. Gregg.
U.S. Appl. No. 12/567,966, filed Sep. 28, 2009, Craig A. Keller.
U.S. Appl. No. 12/613,876, filed Nov. 6, 2009, Craig A. Keller.
U.S. Appl. No. 12/619,234, filed Nov. 16, 2009, James A. Gilbert.
U.S. Appl. No. 12/639,210, filed Dec. 16, 2009, Jennifer S. Harper.
U.S. Appl. No. 12/712,712, filed Feb. 25, 2010, Mani N. Prakash.
U.S. Appl. No. 12/713,956, filed Feb. 26, 2010, Robert B. Smith.
U.S. Appl. No. 12/715,212, filed Mar. 1, 2010, Robert J. Behnke, II.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter, Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.

(56) References Cited

OTHER PUBLICATIONS

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 123 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10191319.2 dated Feb. 22, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.

* cited by examiner

SYSTEM AND METHOD FOR DETECTING AND SUPPRESSING ARC FORMATION DURING AN ELECTROSURGICAL PROCEDURE

BACKGROUND

1. Technical Field

The present disclosure relates to an electrosurgical system and method and, more particularly, to arc detection and suppression for electrosurgical tissue treatment procedures such as vessel sealing and tissue ablation.

2. Background of Related Art

Energy-based tissue treatment is well known in the art. Various types of energy (e.g., electrical, ohmic, resistive, ultrasonic, microwave, cryogenic, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes.

Electrical arc formation is a discharge of current that is formed when a strong current flows through normally non-conductive media such as air (e.g., a gap in a circuit or between two electrodes). Electrical arc formation is problematic when occurring at the site of tissue being treated during an electrosurgical procedure. The arcing results in increased current being drawn from the electrosurgical generator to the electrical arc, thereby increasing the potential of damage to tissue due to the presence of increased levels of current and to the electrosurgical generator due to overcurrent conditions.

SUMMARY

According to an embodiment of the present disclosure, a method for suppressing arc formation during an electrosurgical tissue treatment procedure includes the steps of supplying pulsed current from an energy source to tissue and measuring the pulsed current supplied from the energy source. The method also includes the steps of comparing an instantaneous measured pulse to a predetermined threshold and controlling the pulsed current supplied from the energy source based on the comparison between the instantaneous measured pulse and the predetermined threshold.

According to another embodiment of the present disclosure, a method for suppressing arc formation during an electrosurgical tissue treatment procedure includes the steps of supplying pulsed current from a current source to tissue and measuring each pulse of the supplied pulsed current. The method also includes the steps of comparing each measured pulse to a predetermined threshold and terminating each measured pulse if the measured pulse exceeds the predetermined threshold.

According to another embodiment of the present disclosure, an electrosurgical system includes an electrosurgical generator adapted to supply pulsed current to an electrosurgical instrument for application to tissue and a current limiting circuit operably coupled to the electrosurgical generator and configured to measure each pulse of the pulsed current for comparison with a predetermined threshold. Each pulse is controlled based on the comparison.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1A:
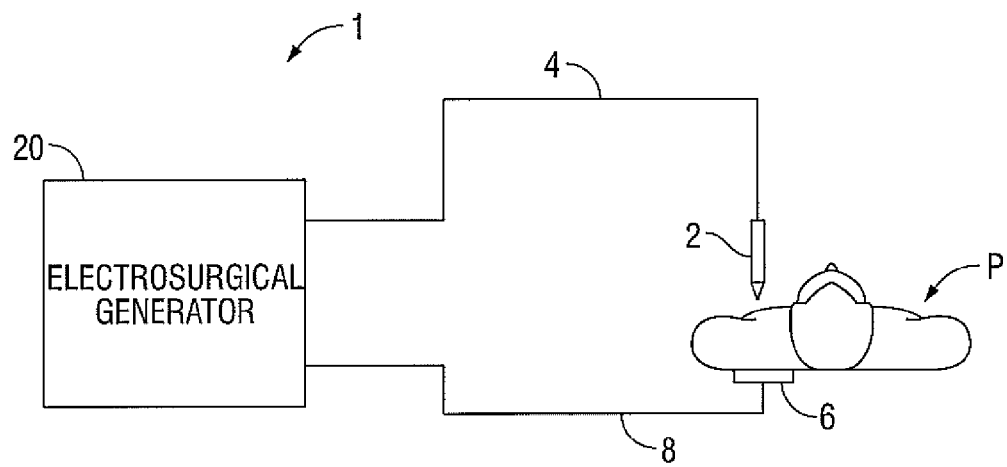
FIG. 1A is a schematic block diagram of a monopolar electrosurgical system in accordance with an embodiment of the present disclosure.

Fig. 1A is a schematic illustration of a monopolar electrosurgical system 1 according to one embodiment of the present disclosure. The system 1 includes an electrosurgical instrument 2 (e.g., monopolar) having one or more electrodes for treating tissue of a patient P (e.g., electrosurgical cutting, ablation, etc.). More particularly, electrosurgical RF energy is supplied to the instrument 2 by a generator 20 via a supply line 4, which is connected to an active terminal 30 (see FIG. 2) of the generator 20, allowing the instrument 2 to coagulate, seal, ablate and/or otherwise treat tissue. The energy is returned to the generator 20 through a return electrode 6 via a return line 8 at a return terminal 32 of the generator 20 (see FIG. 2). The active terminal 30 and the return terminal 32 are connectors configured to interface with plugs (not explicitly shown) of the instrument 2 and the return electrode 6, which are disposed at the ends of the supply line 4 and the return line 8, respectively.

Figure 1B:
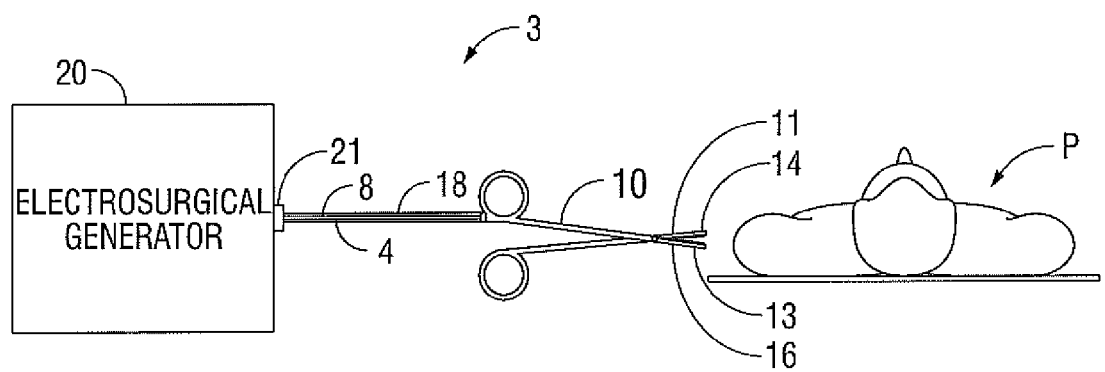
FIG. 1B is a schematic block diagram of a bipolar electrosurgical system in accordance with an embodiment of the present disclosure.

FIG. 1B is a schematic illustration of a bipolar electrosurgical system 3 according to the present disclosure. The system 3 includes a bipolar electrosurgical forceps 10 having one or more electrodes for treating tissue of a patient P. The electrosurgical forceps 10 includes opposing jaw members 11 and 13 having an active electrode 14 and a return electrode 16, respectively, disposed therein. The active electrode 14 and the return electrode 16 are connected to the generator 20 through cable 18, which includes the supply and return lines 4, 8 coupled to the active terminal 30 and return terminal 32, respectively (see FIG. 2). The electrosurgical forceps 10 is coupled to the generator 20 at a connector 21 having connections to the active terminal 30 and return terminal 32 (e.g., pins) via a plug disposed at the end of the cable 18, wherein the plug includes contacts from the supply and return lines 4, 8.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform parameters (e.g., crest factor, duty cycle, etc.), and other parameters to achieve the desired waveform suitable for a particular task (e.g., coagulating, tissue sealing, intensity setting, etc.).

Figure 2:
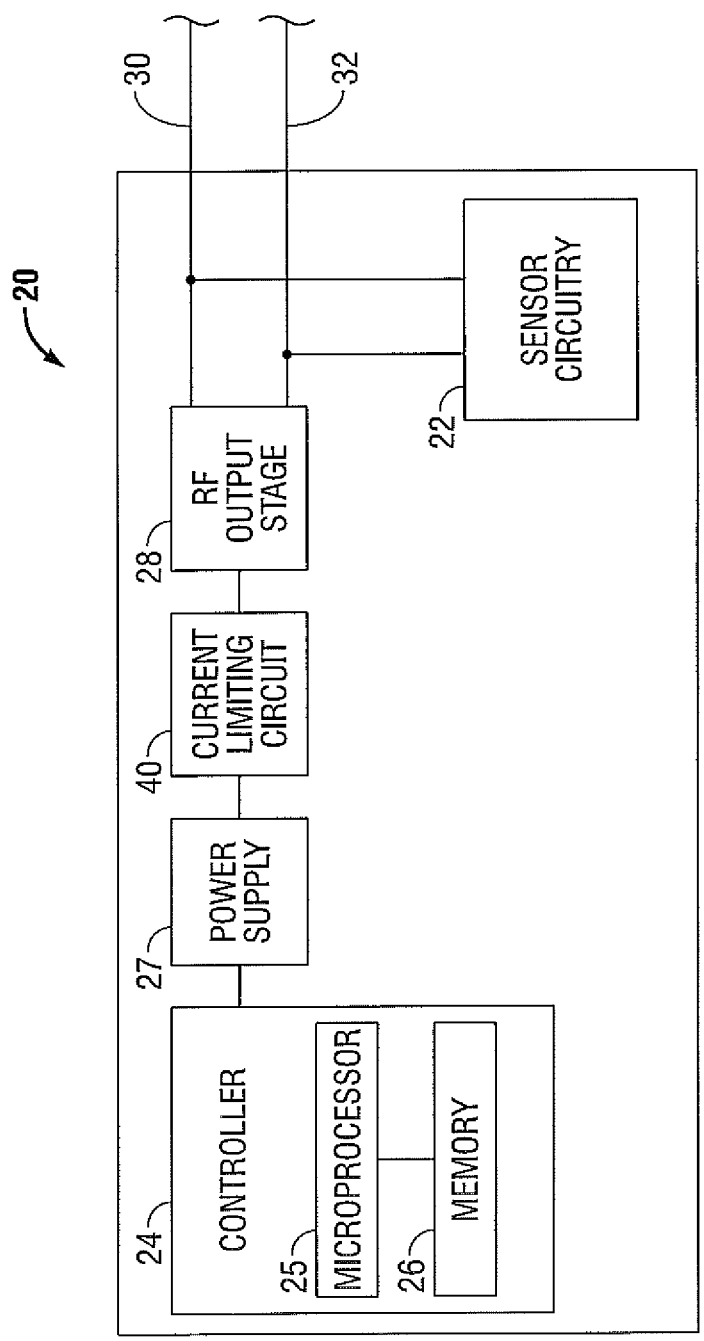
FIG. 2 is a schematic block diagram of a generator in accordance with an embodiment of the present disclosure.

FIG. 2 shows a schematic block diagram of the generator 20 having a controller 24, a DC power supply 27, and an RF output stage 28. The power supply 27 is connected to a conventional AC source (e.g., electrical wall outlet) and is adapted to provide high voltage DC power to an RF output stage 28 that converts high voltage DC power into RF energy. RF output stage 28 delivers the RF energy to an active terminal 30. The energy is returned thereto via the return terminal 32.

The generator 20 may include a plurality of connectors to accommodate various types of electrosurgical instruments (e.g., instrument 2, electrosurgical forceps 10, etc.). Further, the generator 20 may be configured to operate in a variety of modes such as ablation, monopolar and bipolar cutting coagulation, etc. The generator 20 may also include a switching mechanism (e.g., relays) to switch the supply of RF energy between the connectors, such that, for example, when the instrument 2 is connected to the generator 20, only the monopolar plug receives RF energy.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the power supply 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme or feedback control loop is provided that includes sensor circuitry 22 having one or more sensors for measuring a variety of tissue and energy properties (e.g., tissue impedance, tissue temperature, output current and/or voltage, etc.). The sensor circuitry 22 provides feedback to the controller 24. Such sensors are within the purview of those skilled in the art. The controller 24 then signals the HVPS 27 and/or RF output phase 28 which then adjust DC and/or RF power supply, respectively. The controller 24 also receives input signals from the input controls of the generator 20 or the instrument 10. The controller 24 utilizes the input signals to adjust power outputted by the generator 20 and/or performs other control functions thereon.

In particular, sensor circuitry 22 is adapted to measure tissue impedance. This is accomplished by measuring voltage and current signals and calculating corresponding impedance values as a function thereof at the sensor circuitry 22 and/or at the microprocessor 25. Power and other energy properties may also be calculated based on collected voltage and current signals. The sensed impedance measurements are used as feedback by the generator 20. In embodiments, sensor circuitry 22 may be operably coupled between RF output stage 28 and active terminal 30.

A current limiting circuit 40 is operably coupled between the power supply 27 and the RF output stage 28 and is configured to instantaneously control the pulsed current output of power supply 27 on a pulse-by-pulse basis. More specifically, the current limiting circuit 40 is configured to monitor the pulsed current output of power supply 27 and, for each output pulse, the current limiting circuit 40 measures the instantaneous current of the pulse and compares the measured instantaneous current to a predetermined threshold current. In some embodiments, the predetermined threshold current may be the maximum allowable current output of the power supply 27. If the measured instantaneous current exceeds the predetermined threshold current, the current limiting circuit 40 controls the pulsed current output of power supply 27 and/or terminates the measured pulse, as will be discussed in further detail below with reference to FIGS. 3 and 4.

In one embodiment, current limiting circuit 40 includes suitable components preconfigured to measure instantaneous current on a pulse-by-pulse basis and control (e.g., adjust, terminate, suspend, etc.) output of generator 20 based on a comparison between the measured current and the predetermined threshold current, as will be discussed in detail below. For example, in some embodiments, the predetermined threshold current may be between about 4.5 A and about 6 A. In another embodiment, the predetermined threshold current may be, for example, data stored in memory 26 and configured to be compared to each current pulse measured by current limiting circuit 40 for processing by microprocessor 25. Based on this comparison, the microcontroller 25 generates a signal to controller 24 to control the pulsed output current of generator 20.

Figure 3:
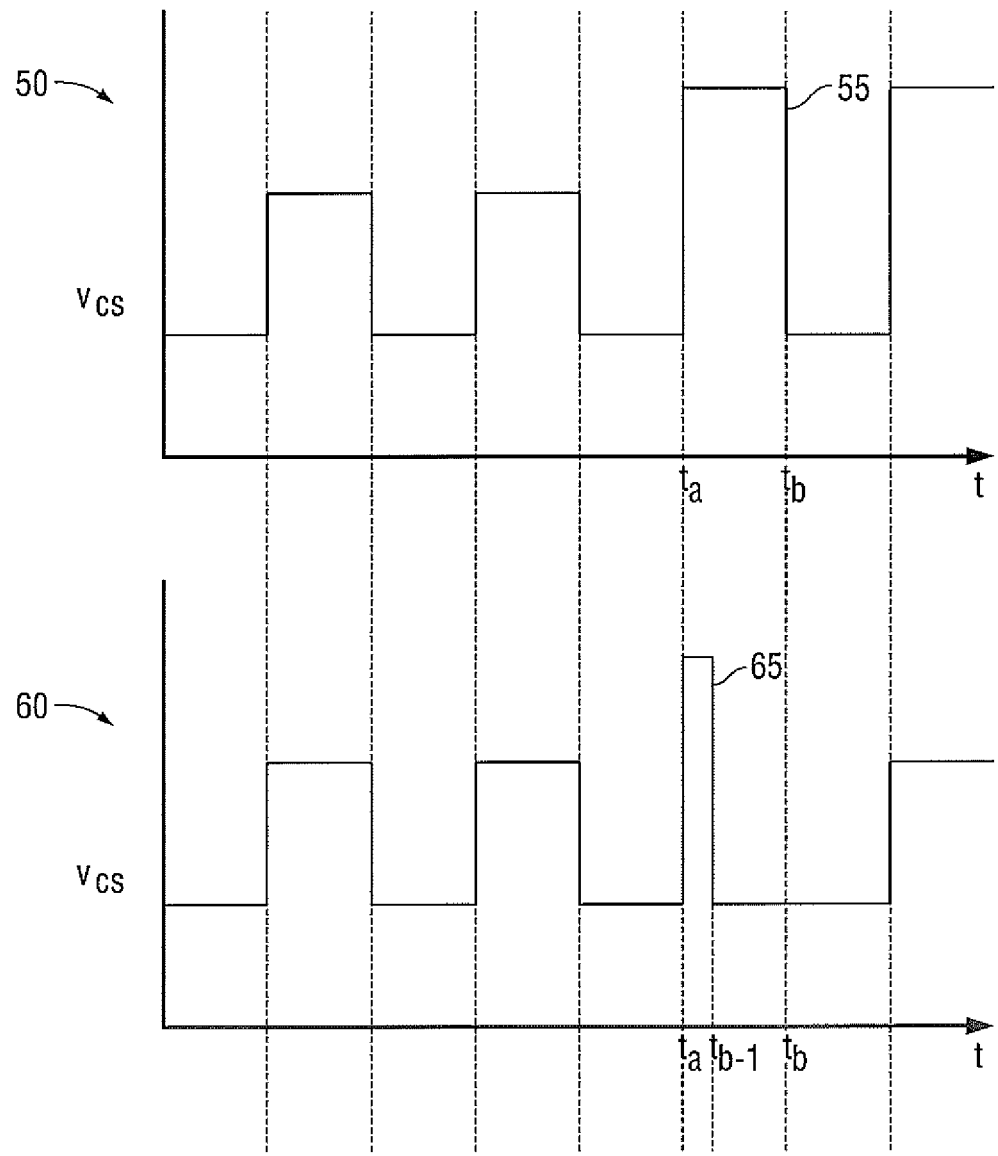
FIG. 3 illustrates a relationship between current source voltage vs. time for tissue undergoing treatment in accordance with two contrasting scenarios.

FIG. 3 illustrates the relationship between a current source voltage $v_{cs}$ (e.g., the voltage across power supply 27) vs. time "t" waveform 50, wherein current limiting circuit 40 is not utilized, and a corresponding current voltage source $v_{cs}$ vs. time "t" waveform 60 taken over the same time range as waveform 50, wherein current limiting circuit 40 is utilized in accordance with embodiments described by the present disclosure. Waveforms 50 and 60 illustrate, by way of example, the pulsed output current of generator 20 resulting from the contrasting scenarios discussed above. Waveform 50 is illustrated for purposes of contrast with waveform 60 (described below) to show the benefit of using current limiting circuit 40 to detect and suppress electrical arc formation at the tissue site. Electrical arc formation at the site of the tissue being treated results in increased current being drawn from the generator 20 to the electrical arc, thereby increasing the potential of damage to tissue caused by the presence of increased current and to the generator 20 due to overcurrent conditions.

Waveform 50 illustrates the pulsed output current of RF output stage 28 including an abnormal pulse 55 that represents a significantly increased voltage $v_{cs}$ between time intervals $t_a$ and $t_b$. As described above, the abnormal pulse 55 may be caused by the occurrence of electrical arcing at the tissue site that results in increased current drawn from power supply 27 to the electrical arc and, thus, an increase in voltage $v_{cs}$, for the duration of pulse 55 (e.g., time interval $t_a \leq$ time "t" $\leq$ time interval $t_b$).

Similar to waveform 50, waveform 60 illustrates the pulsed output current of power supply 27 including an abnormal pulse 65 that represents a significantly increased voltage $v_{cs}$ starting at time interval $t_a$ similar to abnormal pulse 55 discussed above. However, in this instance, the abnormal pulse 65 is instantaneously detected by current limiting circuit 40, and terminated at time interval $t_{b-1}$. More specifically, the abnormal pulse 65 is measured and compared to the predetermined threshold current, and terminated at time interval $t_{b-1}$ since the measured pulse exceeds the predetermined threshold current. This is in contrast to the duration of abnormal pulse 55, which without the benefit of detection and termination via current limiting circuit 40 endures from time interval $t_a$ to time interval $t_b$. Since the above described comparison is repeated for each pulse, the current limiting circuit 40 of the present disclosure operates to regulate the duty cycle and, thus, the RMS current of the pulsed current output of the generator 20 to prevent or suppress arc formation, thereby minimizing potential damage to tissue from increased drawing of current to the electrical arc.

Current limiting circuit 40 may include any suitable components to enable operation as described hereinabove such as, for example, current sense resistors, shunt resistors, transistors, diodes, switching components, transformers, and the like. Although shown in the illustrated embodiments as being operably coupled between power supply 27 and RF output stage 28, current limiting circuit 40 may be integrated within power supply 27 or RF output stage 28 or may be operably coupled between RF output stage 28 and active terminal 30.

Figure 4:
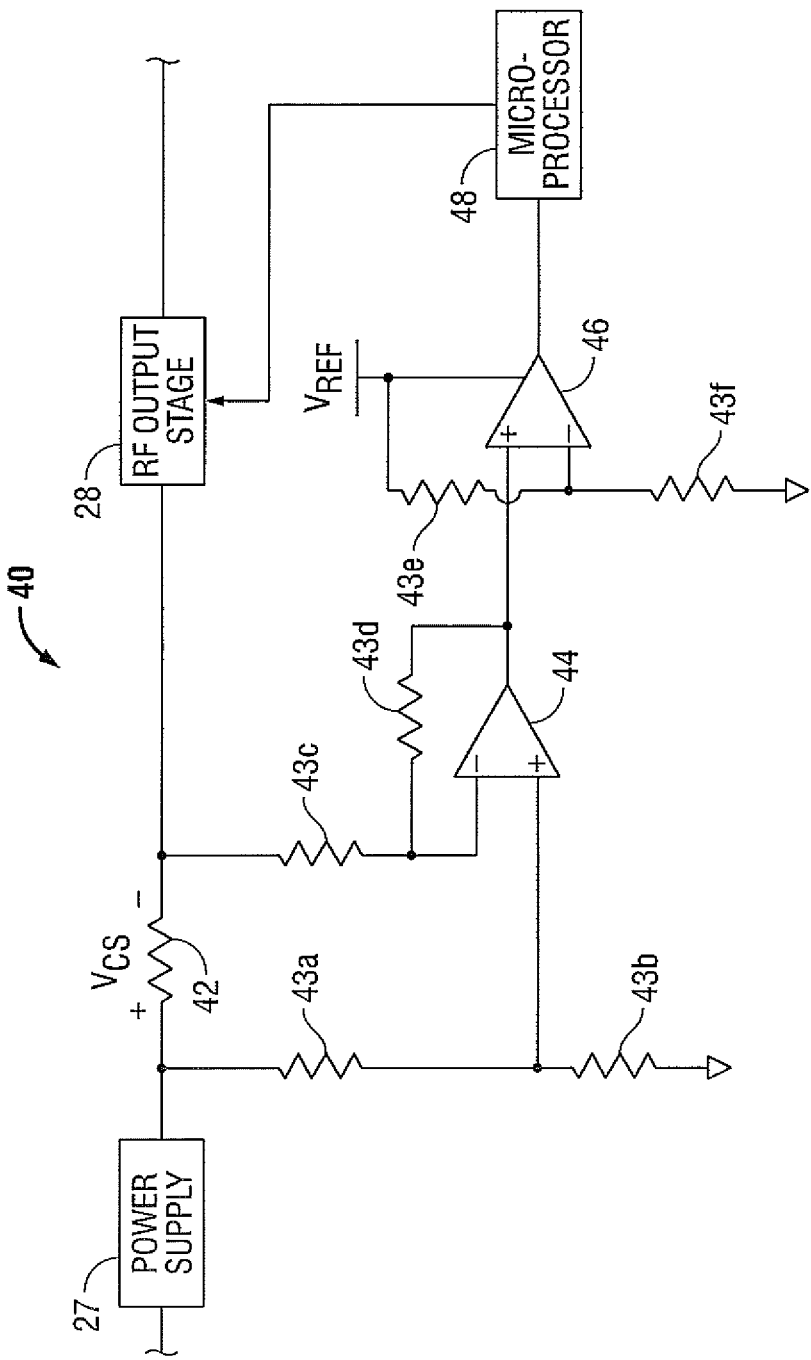
FIG. 4 is a circuit diagram of a current limiting circuit according to an embodiment of the present disclosure.

FIG. 4 shows, by way of example, a circuit schematic of current limiting circuit 40 according to some embodiments of the present disclosure. In this example, current limiting circuit 40 includes a current sense resistor 42 that operates in conjunction with an op-amp 44, a comparator 46, a plurality of resistors 43a-f, and a microprocessor 48, to control the pulsed current output of power supply 27 that is supplied to instrument 2 or forceps 10 on a pulse-by-pulse basis, as discussed hereinabove.

As power supply 27 supplies pulsed current to RF output stage 28, a potential difference $V_{cs}$ is generated across current sense resistor 42 and received, as input, at the non-inverting or positive input of op-amp 44. $V_{cs}$ is proportional to the pulsed current output of power supply 27. Op-amp 44 generates an output voltage signal that is fed back to the inverting or negative input of op-amp 44 (e.g., negative feedback), causing op-amp 44 to drive its output voltage signal toward a level that minimizes the differential voltage between its positive and negative inputs. The output voltage signal of op-amp 44 is received, as input, at the positive input of comparator 46. A reference voltage $V_{REF}$ (e.g., 3.3 volts) that is proportional to the predetermined threshold current is applied to the negative input of comparator 46 for comparison to the input voltage signal received from op-amp 44. In this way, the pulsed current output of power supply 27 is compared to the predetermined threshold current on a pulse-by-pulse basis by way of comparison, at comparator 46, between $V_{REF}$ and the input voltage signal from op-amp 44. This comparison dictates the output of comparator 46, which will change either from "high" to "low" or from "low" to "high" as the input voltage signal from op-amp 44 exceeds $V_{REF}$. The "high" or "low" output of comparator 46 signals microprocessor 48 to control the output of RF output stage 28 accordingly. As the input voltage signal from op-amp 44 exceeds $V_{REF}$ comparator 46 signals the microprocessor 48 to cause RF output stage 28 to interrupt or terminate the instantaneous current pulse (e.g., pulse 65) being supplied to instrument 2 or forceps 10. For example, in some embodiments, RF output stage 28 includes one or more suitable switching components (not shown) such as a transistor that opens or closes in response to an output signal (e.g., turn-on voltage) received from microprocessor 48. In this scenario, when the switching component is closed, the pulsed current output of power supply 27 is delivered un-interrupted to instrument 2 or forceps 10 via RF output stage 28 and, when the switching component is open, the pulsed current output of power supply 27 is shunted to ground through resistors 43a and 43b rather than being supplied to instrument 2 or forceps 10. The termination or interruption of an instantaneous current pulse being supplied to instrument 2 or forceps 10 operates to suppress or terminate electrical arcing that may be formed at the tissue site. By terminating the instantaneous current pulse, the voltage $V_{Cs}$ across the current sense resistor 42 decreases below $V_{REF}$ such that the output voltage signal from op-amp 44 is less than $V_{REF}$ by comparison. The resulting output of comparator 46 operates to signal the RF output stage 28 to continue or re-establish (e.g., via closing of the switching component) delivery of pulsed current output from power supply 27 to instrument 2 or forceps 10 for application to tissue. In this way, current limiting circuit 40 controls on a pulse-by-pulse basis whether or not pulsed current is supplied to instrument 2 or forceps 10.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for suppressing arc formation during an electrosurgical tissue treatment procedure, comprising:
    supplying a plurality of pulses from an energy source to tissue, each pulse of the plurality of pulses configured to be active for a duration of time;
    instantaneously measuring each pulse of the plurality of pulses supplied from the energy source;
    comparing the instantaneous measurement to a predetermined threshold within the duration of time of each pulse;
    reducing the duty cycle of the plurality of pulses supplied from the energy source based on the comparison between the instantaneous measurement and the predetermined threshold; and
    terminating each pulse prior to completion of the duration of time based on the comparison between the instantaneous measurement and the predetermined threshold.

2. The method according to claim 1, further comprising terminating each pulse based on the instantaneous measurement exceeding the predetermined threshold.

3. The method according to claim 1, further comprising reducing the duty cycle of the plurality of pulses based on the instantaneous measurement exceeding the predetermined threshold.

4. The method according to claim 1, further comprising using a current limiting circuit operably coupled to the energy source to perform at least one of the measuring, comparing, or reducing.

5. The method according to claim 1, further comprising comparing a first voltage proportional to the predetermined threshold to a second voltage proportional to the plurality of pulses from the energy source.

6. The method according to claim 5, wherein the plurality of pulses are controlled based on the second voltage exceeding the first voltage.

7. The method according to claim 1, further comprising generating a signal based on the comparison between the instantaneous measurement and the predetermined threshold and transmitting the signal to a controller operably coupled to the energy source, the controller configured to control the duty cycle of the plurality of pulses supplied from the energy source based on the signal.

8. The method according to claim 1, wherein the predetermined threshold is a maximum allowable current output of the energy source.

9. A method for suppressing arc formation during an electrosurgical tissue treatment procedure, comprising:
   supplying pulsed current from a current source to tissue, each pulse of the supplied pulsed current configured to be active for a duration of time;
   measuring each pulse of the supplied pulsed current;
   comparing each measured pulse to a first predetermined threshold and a second predetermined threshold during the duration of time;
   terminating each measured pulse if the measured pulse exceeds the first predetermined threshold prior to completion of the duration of time; and
   reducing a duty cycle of the pulsed current supplied from the current source if the measured pulse exceeds the second predetermined threshold.

10. The method according to claim 9, further comprising using a current limiting circuit operably coupled to the current source to perform at least one of the measuring, comparing, terminating, or reducing.

11. The method according to claim 9, further comprising comparing a first voltage proportional to the first predetermined threshold to a second voltage proportional to the pulsed current from the current source.

12. The method according to claim 11, wherein the pulsed current is terminated based on the second voltage exceeding the first voltage.

13. The method according to claim 9, further comprising generating a signal based on the comparison between each measured pulse and the first predetermined threshold and transmitting the signal to a controller operably coupled to the current source and configured to control the current source based on the signal.

* * * * *